United States Patent [19]

Davis

[11] 4,167,402
[45] Sep. 11, 1979

[54] ETHYLENE SEPARATION PROCESS

[75] Inventor: James S. Davis, North Tonawanda, N.Y.

[73] Assignee: Union Carbide Corporation, New York, N.Y.

[21] Appl. No.: 888,222

[22] Filed: Mar. 20, 1978

Related U.S. Application Data

[63] Continuation-in-part of Ser. No. 833,827, Sep. 16, 1977, abandoned.

[51] Int. Cl.² ............................................... F25J 3/02
[52] U.S. Cl. ........................................ 62/28; 62/26; 62/18
[58] Field of Search ............................. 62/26, 28, 23

[56] References Cited

U.S. PATENT DOCUMENTS

| | | | |
|---|---|---|---|
| 2,500,353 | 3/1950 | Gantt | 62/28 |
| 3,073,130 | 1/1963 | Becker | 62/28 |
| 3,186,182 | 6/1965 | Grossman et al. | 62/28 |
| 3,319,428 | 5/1967 | Isaacson | 62/28 |
| 3,373,574 | 3/1968 | Fisher | 62/28 |
| 3,524,897 | 8/1970 | Kniel | 62/28 |
| 3,675,435 | 7/1972 | Jackson et al. | 62/28 |

*Primary Examiner*—Norman Yudkoff
*Attorney, Agent, or Firm*—Steven J. Hultquist

[57] ABSTRACT

A process for separating a hydrocarbon feed gas mixture comprising at least $C_1$–$C_2$ constituents including ethylene to produce a separated ethylene product. The disclosed process employs a recovery section in which demethanization is carried out at moderate pressure, thereby permitting efficient and economical use of propylene-ethylene refrigeration in the process.

11 Claims, 4 Drawing Figures

ETHYLENE SEPARATION PROCESS

CROSS-REFERENCE TO RELATED APPLICATION

This is a continuation-in-part of U.S. Ser. No. 833,827 filed Sept. 16, 1977 now abandoned.

BACKGROUND OF THE INVENTION

1. Field of the Invention

This invention relates to a process for separating a hydrocarbon feed gas mixture comprising at least $C_1$-$C_2$ constituents including ethylene to produce a separated ethylene product.

2. Description of the Prior Art

Ethylene is one of the most important and largest commercial volume petrochemicals in the world today. As a result significant and continuing effort has been expended in the design and development of new and improved ethylene production, recovery, separation and purification methods.

Ethylene is primarily produced by thermal pyrolysis of hydrocarbon fractions. Heretofore, ethane and propane were the prevailing raw materials for ethylene production. However, the presently dwindling supply of these light hydrocarbons is expected to shift the predominant feedstocks for ethylene production to the more available heavier hydrocarbon fractions such as naphtha.

In commercial practice, naphtha feed stocks are pyrolyzed to produce a hydrocarbon gas mixture containing ethylene. To recover the end ethylene product, it is then necessary to separate the ethylene from the remaining hydrocarbon constituents and purify same.

In an ethylene plant, the sequence in which the various separation (fractionation) steps are employed has a significant influence on the capital and operating costs and energy requirements of the ethylene production facility. Pressure levels must be selected for the operation of each fractionation column in the ethylene plant in relation to this sequence and to the operating constraints for permissible column bottom temperatures and column overhead refrigeration levels. In each fractionation operation, there are maximum temperature limits inherent in the process step to avoid polymerization and fouling, and minimum temperature limits to avoid hydrocarbon freezing or formation of hydrate species.

In practice, the prior art has employed both low pressure, e.g., 150-200 psia, and high pressure, e.g., 500-600 psia, ethylene production processes. These processes, however, as they have evolved to date, both possess inherent deficiencies in overall energy utilization. In many instances, low pressure ethylene production processes are attractive since they allow easily facilitated fractionation of the various pyrolysis gas constituents, since lower pressures in general provide higher relative volatilities. In turn, higher relative volatilities permit lower reflux ratios and correspondingly lower condenser heat duties to be employed for the various fractionation columns in the ethylene plant. Nonetheless, the low process temperatures associated with low pressure operation substantially increase the refrigeration load requirements for the ethylene plant and, attendantly, the compression requirements associated with the refrigeration system for the ethylene plant. High pressure operation, on the other hand, overcomes many of the inherent deficiencies associated with low temperature operation, and is generally preferred in practice. Nonetheless, at high operating pressures, the decrease in relative volatilities with the corresponding increas in reflux ratios, which are required to carry out the necessary sparation steps, substantially raise the condenser heat duties for the fractionation columns in the ethylene plant. Relative to the low pressure ethylene production process, the high pressure process has a substantially lower compression requirement associated with the ethylene plant refrigeration system. Despite such relative advantage, the refrigeration system compression requirement in the high pressure process is still large in magnitude and when added to the large compression requirements for the pyrolyzed feed gas mixture yields a high overall compression requirement for the process.

In connection with the foregoing, a significant operating cost in any ethylene production plant is associated with the compression system therefor. There are two functional requirements which the conventional ethylene plant compression system satisfies. First of all, the pyrolyzed hydrocarbon gas mixture must be pressurized to permit acid gas removal, to facilitate the recovery of the heavy hydrocarbon fractions the therefrom, and to minimize the overall refrigeration requirements in recovering the lighter hydrocarbon constituents, including ethylene. Secondly, the refrigeration system in the ethylene plant requires considerable compression energy. In the refrigeration system, the refrigerant fluids undergo a closed cycle of compression and expansion to supply the necessary cold for provision of the heat duty for the condensers of the light hydrocarbon fractionation columns.

In conventional high pressure ethylene plants, wherein the low temperature fractionation steps for separating the constituents of the ethylene-containing hydrocarbon feed gas mixture are conducted at pressure levels on the order of 300-600 psia, the refrigeration for the separation steps is supplied by propylene refrigerant at temperature levels down to about $-40°$ C. and by ethylene refrigerant at levels down to about $-100°$ C.

In low pressure ethylene plants, methane refrigeration has been employed in conjunction with propylene and ethylene refrigerants in cascaded refrigeration systems. Such cascaded systems permit temperatures as low as $-130°$ C. to be achieved and allow the operating pressures of the fractionation steps to be substantially reduced, for example, to 150-200 psia, by virtue of the lower temperatures. Triple-cascaded systems, however, require additional methane refrigeration compressors, and the savings in feed stream compression is not large enough to provide an overall practical advantage for the cascaded system. As a result, methane refrigeration has not been widely used in commercial ethylene plants.

Regarding the fractionation steps of the ethylene plant in greater detail, a variety of process equipment sequences are employed. One widely used sequence incorporates a demethanizer column at the head of the fractionation section followed by deethanizer and $C_2$ splitter columns, depropanizer and $C_3$ splitter columns, debutanizer column, depentanizer column, and other separation equipment as is required. In another arrangement, a depropanizer is positioned at the head of the fractionation section, so that $C_3$'s and lighter are separated from $C_4$'s and heavier initially. This so-called front-end depropanizer scheme generally permits better maintenance of olefin (ethylene) purity specifications, and substantially reduces capital, power, and operating costs over a front end demethanizer arrangement. By separating out the $C_4$'s and heavier initially, the subsequent separation equipment can operate at extremely low temperatures without the problems arising from freezing of heavy hydrocarbon constituents. Operation at such extremely low temperature levels allows particularly efficient light component separations to be carried out. Similar advantages can be obtained in arrangements using a front-end deethanizer for initial removal of $C_3$'s and heavier from the hydrocarbon feed gas mixture. In one particularly efficient arrangement for a front-end depropanizer or a front-end deethanizer system, the light components in the depropanizer or deethanizer overhead stream are separated and removed in a forecooling recovery section operating at low temperature, with the remaining ethylene-bearing streams passing to the final separation section. In all of these various arrangements, despite the fact that some savings in refrigeration system compression requirements can be effected by operation at high pressure as compared with low pressure, the ethylene plant has associated therewith extremely large compression system energy requirements.

Accordingly, it is an object of the present invention to provide an improved ethylene production process.

It is another object of the invention to provide an ethylene separation process which is adaptable to a high pressure hydrocarbon feed gas mixture and employs a separation section in which demethanization is carried out at moderate pressure, thereby effecting significant savings in refrigeration compression requirements relative to conventional high pressure ethylene separation processes.

It is another object of the invention to provide an ethylene separation process which substantially reduces the overall operating pressure and hence the total compression energy requirements below the levels associated with prior art high pressure ethylene production processes, while employing only propylene-ethylene refrigeration.

Other objects and advantages of the invention will be apparent from the ensuing disclosure and appended claims.

SUMMARY OF THE INVENTION

The present invention relates to a process for separating a hydrocarbon feed gas mixture comprising at least $C_1$–$C_2$ constituents including ethylene to produce a separated ethylene product.

In the process of this invention, the hydrocarbon feed gas mixture is provided at superatmospheric pressure between 200 and 700 psia, cooled to condense a first liquid fraction comprising at least $C_1$–$C_2$ constituents, and the first liquid fraction is separated from the uncondensed gas.

The first liquid fraction is fractionated in a demethanizer column at superatmospheric pressure of 100–350 psia to recover a demethanizer overhead comprising methane and a demethanizer bottoms comprising at least $C_2$ constituents. The demethanizer bottoms are fractionated to recover ethylene as overhead product and ethane bottoms. The uncondensed gas from which the first liquid fraction has been separated is further cooled at high superatmospheric pressure of at least 350 psia to condense a second liquid fraction comprising $C_1$–$C_2$ constituents, and the second liquid fraction is separated from the uncondensed further cooled gas. The second liquid fraction is throttled to low superatmospheric pressure below 200 psia. The throttled second liquid fraction is mixed with the demethanizer overhead to form a fluid mixture comprising $C_1$–$C_2$ constituents. $C_1$ constituents are stripped from the fluid mixture by methane-containing vapor in a stripping zone to recover methane-rich vapor overhead and bottoms liquid containing methane and $C_2$ constituents. The stripping zone bottoms liquid is partially vaporized to form the aforementioned methane-containing vapor for the stripping zone. Unvaporized stripping zone bottoms liquid is separated from the vaporized methane-containing vapor. The latter is passed to the stripping zone as the methane-containing vapor therefor and the unvaporized stripping zone bottoms liquid is passed to the demethanizer column for fractionation therein with the first liquid fraction.

In a particularly preferred embodiment of the present invention, the fractionation of demethanizer bottoms to recover ethylene as overhead product and ethane bottoms comprises providing a $C_2$ fractionation column comprising a first rectification zone, a second rectification zone having a lower end in direct heat transfer communication with an upper end of the first rectification zone, and a third rectification zone having a lower end in direct heat transfer communication with an upper end of the second rectification zone. The demethanizer bottoms are rectified in the first rectification zone to recover ethylene-rich overhead and ethane-rich bottoms. The ethane-rich bottoms recovered from the first rectification zone is throttled to lower superatmospheric pressure. The throttled ethane-rich bottoms recovered from the first rectification zone is rectified in the second rectification zone to recover ethylene-rich overhead and ethane-rich bottoms. The ethane-rich bottoms recovered from the second rectification zone is throttled to still lower superatmospheric pressure. The throttled ethane-rich bottoms recovered from the second rectification zone is rectified in the third rectification zone to recover ethylene overhead and ethane bottoms. The ethylene-rich overhead recovered from the first rectification zone and the ethylene-rich overhead recovered from the second rectification zone are throttled to the still lower superatmospheric pressure, cooled, and passed to an upper end of the third rectification zone as reflux to enhance the rectification therein.

As used herein the term "recover" or "recovered stream" will be understood to relate to an overhead or bottoms stream which is discharged from a given separation column subsequent to the associated respective reflux condensing or reboil vaporizing operations. The terms "gas" and "gaseous" will be understood to refer to both gases and vapors.

DESCRIPTION OF THE PREFERRED EMBODIMENT

Figure 1A:
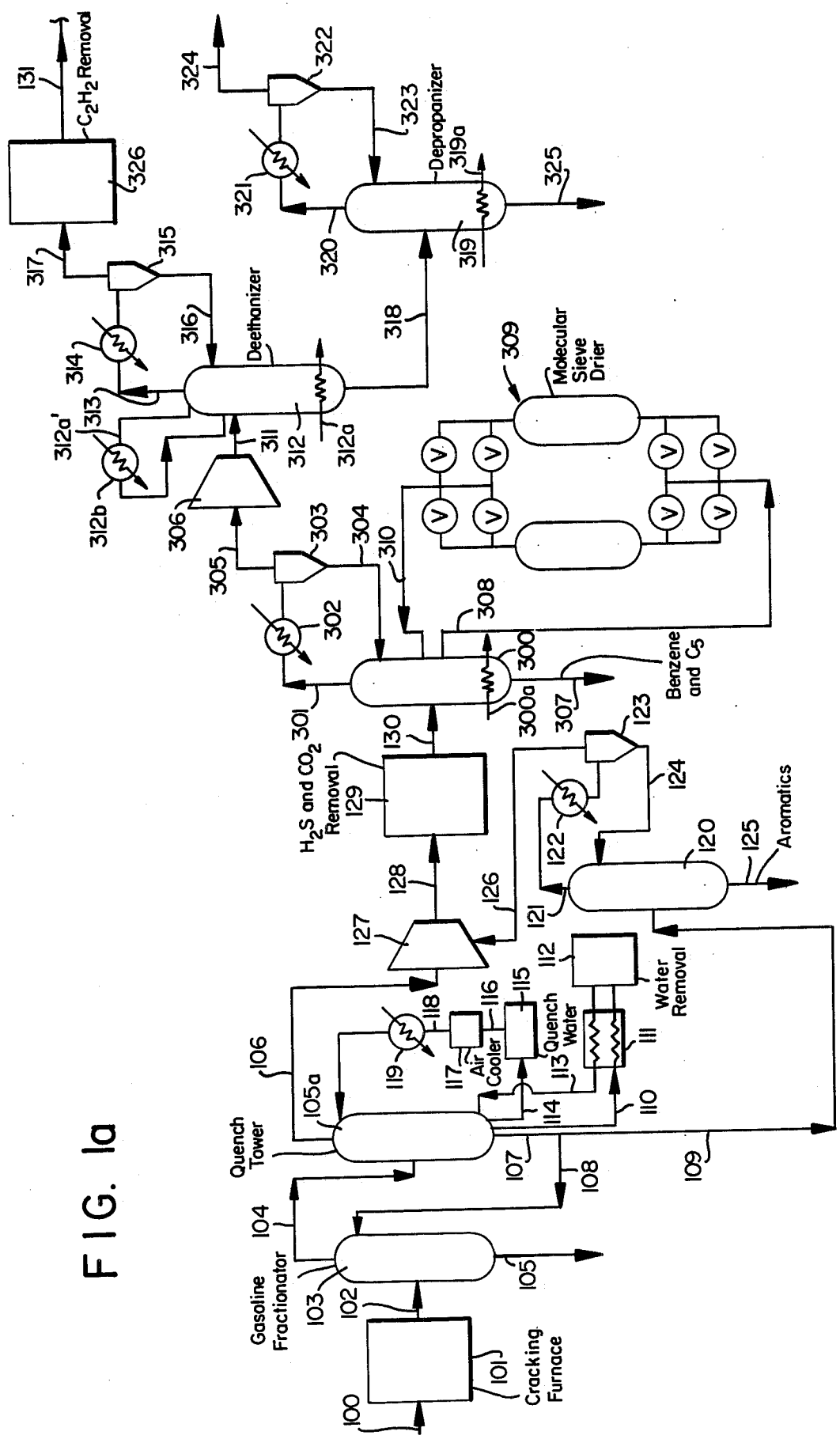
FIGS. 1a, 1b and 1c are consecutive sections of a flow sheet embodying a process according to the present invention.
Figure 1B:
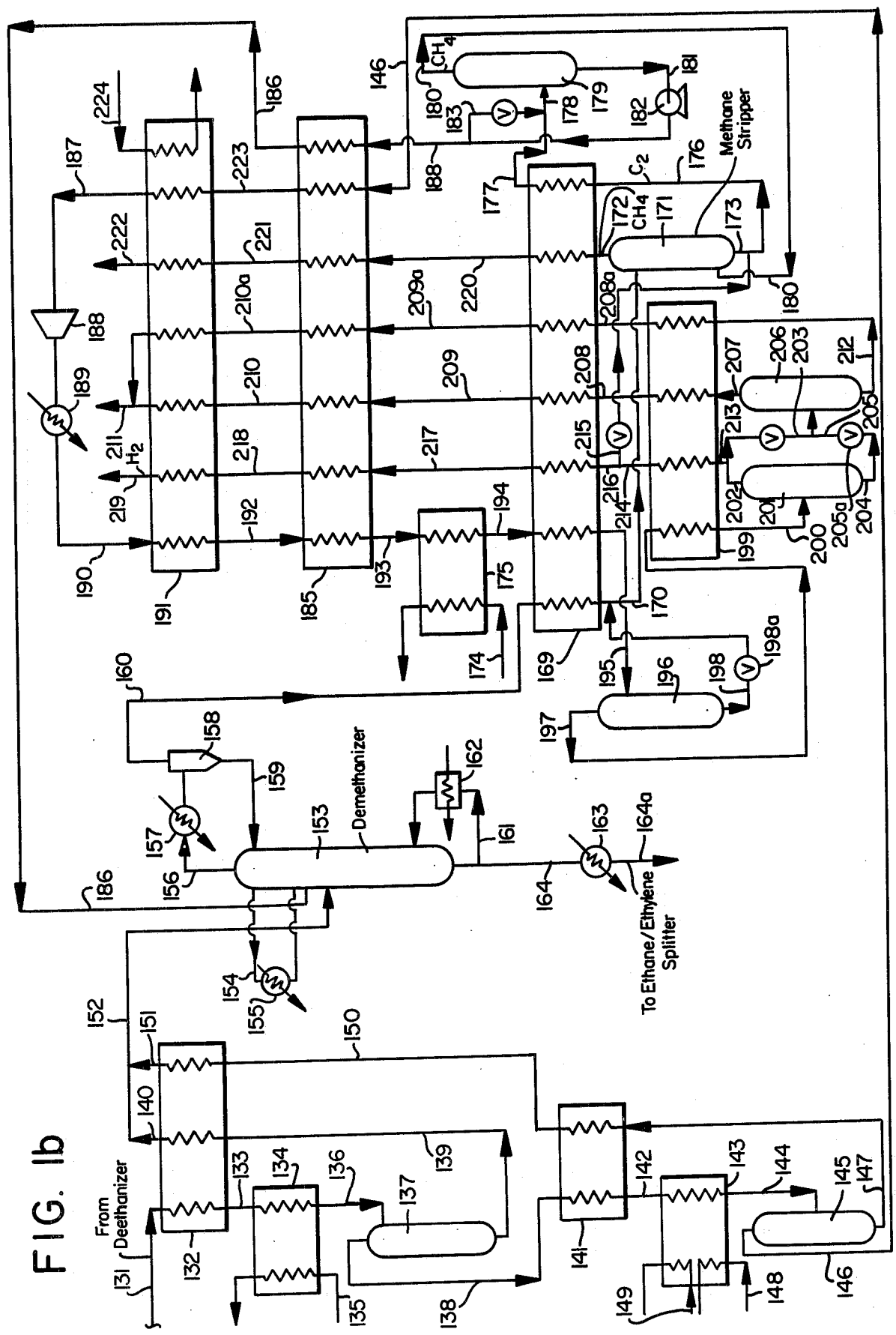
Figure 1C:
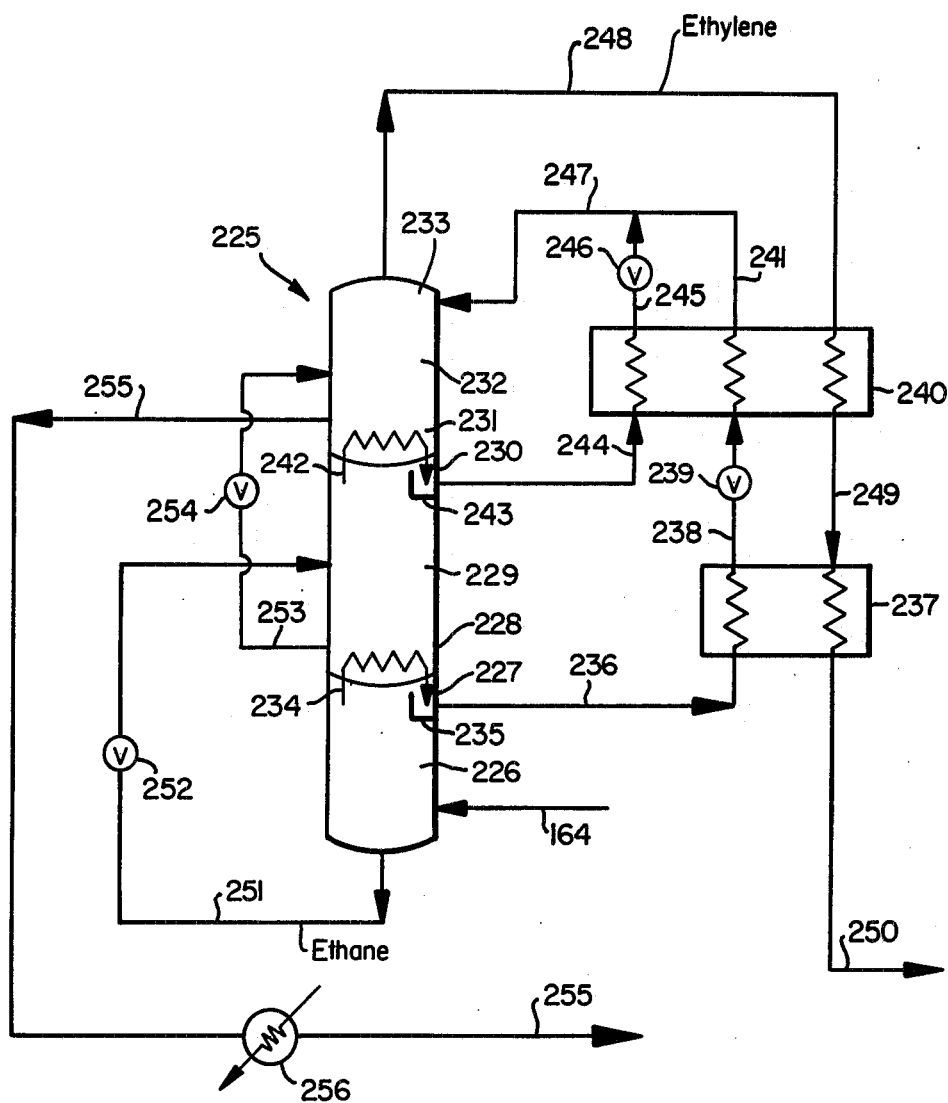

Referring now to the drawings, FIGS. 1a, 1b, and 1c are consecutive sections of a flowsheet embodying a process according to the invention. The following description will be based on the processing of a light naptha hydrocarbon feedstock having a paraffin content of 85%, a napthalenes content of 12% and an aromatics content of 3%, having a specific gravity of 0.68 and a hydrogen to carbon ratio of 2.25. The light naptha feed mixture enters the process through line 100 and passes into the treatment complex 101 for cracking and cooling therein in a manner well known to those skilled in the art. Cracking is usually carried out in high temperature furnaces wherein endothermic pyrolysis and dehydrogenation reactions occur to yield an ethylene-rich hydrocarbon gas mixture. The ethylene-containing hot gases from the cracking furnace are thereafter indirectly heat exchanged (cooled) with boiler feed water to prevent further reaction, thereby generating high pressure steam which is used to drive the various compressors in the ethylene plant. The cracked hydrocarbon gas mixture is discharged from the treatment complex 101 in line 102 at a flow rate of 16,365 kg—moles/hr., a pressure of 36 psia (0.70 kg/cm$^2$), and a temperature of 425° C., with the following approximate molar composition: $H_2$=6.97%, $CH_4$=13.06%, $C_2H_6$ 2.74%, $C_2H_4$=12.74%, $C_3$ constituents=4.55%, water=54.26% and the remainder mainly $C_4$ and heavier constituents.

The cracked hydrocarbon gas mixture in line 102 is passed to gasoline fractionator column 103 for further quenching and fractionation therein to recover fuel oil bottoms in line 105. The overhead from the gasoline fractionator in line 104, depleted in fuel oil constituents, is passed to the quench tower 105a for hydrocarbon gas mixture cooling from temperature of 95° C. (206° F.) to approximately 37° C. (98° F.). The quench tower may suitably contain a multiplicity of vertically spaced-apart gas-liquid contacting trays, of a type well known to those skilled in the art. A heavy hydrocarbon bottoms is recovered from the quench tower in line 107; a portion thereof is returned in line 108 to gasoline fractionator 103, to enhance the fractionation therein. The remainder, in line 109, is passed to the dripstill column 120. Bottoms are also removed from the quench tower in line 110 and passed through heat exchanger 111 for cooling therein, with subsequent treatment in the water removal complex 112, in which water is stripped from the bottoms liquid. Water-depleted bottoms are then returned in line 113 through heat exchanger 111 for warming therein, and are recycled to the quench tower 105a. An additional bottom stream is removed from the lower portion of the quench tower 105 in line 114. This latter bottom stream, which contains a major portion of water, is passed into complex 115 for quench water usage and is then passed in line 116 to the trim air cooler 117 wherein the bottoms fluid is mechanically cooled. The cooled bottoms fluid is then passed in line 118 through heat exchanger 119 for further cooling therein by cooling water and is returned to the upper portion of the quench tower 105a to enhance the quenching operation therein. Overhead is removed from the quench tower in line 106 at a flow rate of 8,468 kg—moles/hr, a pressure of 20 psia (0.39 kg/cm$^2$) a temperature of 37.3° C., and with the following approximate molar composition: $H_2$=13.47%, $CH_4$=25.23%, $C_2H_6$=5.31%, $C_2H_4$=24.63%, water=4.64% and the remainder mainly $C_3$'s and heavier constituents. The overhead gas from the quench tower is then compressed in the furnace gas compression complex 127 to a pressure of 162 psia (10.32 kg/cm$^2$). Compression complex 127 may suitably consist of three stages of compression, with cooling and liquid removal after each stage in a conventional manner, The bottoms from the quench tower in line 109 are fractionated in dripstill 120 to recover bottoms liquid containing a high fraction of aromatic constituents in line 125 which are recycled to aromatics recovery operations and other end uses. Overhead vapor from the drip still column in line 121 is partially condensed by cooling in heat exchanger 122 by propylene refrigerant and is then phase separated in phase separator 123. Condensed liquid from phase separator 123 is recycled as reflux to the drip still column in line 124. Uncondensed vapor overhead recovered from the column in line 126 is introduced to the furnace gas compression complex 127 for compression therein to the aforementioned high pressure of 162 psia.

The combined furnace gas compression effluent in line 128 is passed to the acid gas removal complex 129 wherein acidic components ($H_2S$ and $CO_2$) of the gas mixture are removed, as for example by amine and caustic washing operations in a well-known manner. The hydrocarbon gas mixture, from which acidic components has been removed, is passed in line 130 to $C_4/C_5$ fractionator column 300.

The bottoms from column 300, in line 307, comprise mainly benzene and $C_5$ constituents which are routed to heavy constituent recovery and separation steps. Reboil vapor is generated for the $C_4/C_5$ fractionation column by passage of steam through reboil coil 300a disposed in the lower part of the column. At an intermediate point along the $C_4/C_5$ fractionator column, a vapor stream is withdrawn in line 308 and passed through the drying complex 309, which may suitably comprise two molecular sieve absorbent beds manifolded together in parallel relationship for alternate sequential operation, so that while one absorbent bed is undergoing adsorption, another is being regenerated for further gas treatment. In the adsorption zone, residual water is removed from the hydrocarbon gas mixture, so that an essentially water-free gas mixture is recycled to the $C_4/C_5$ fractionation column in line 310. Overhead vapor from the $C_4/C_5$ fractionation column is discharged from the column in line 301, partially condensed by heat exchange in heat exchanger 302 with propylene refrigerant and phase separated in phase separator 303. Condensed liquid from the phase separator is returned to the column as reflux in line 304. Uncondensed vapor overhead recovered from the column is withdrawn from the phase separator in line 305 and subjected to final gas compression in compressor 306, from a pressure of about 134 psia (8.35 kg/cm$^2$) to approximately 277 psia (18.41 kg/cm$^2$), and the resulting pressurized hydrocarbon feed gas mixture in line 311 is passed to the deethanizer column 312 for fractionization therein to recover overhead gas comprising $C_2$ and the lighter constituents in line 317 and bottoms comprising $C_3$ and heavier constituents in line 318. Overhead from the deethanizer column in line 313 is cooled for partial condensation thereof in heat exchanger 314 against high pressure ethylene refrigerant and phase separated in phase separator 315, with the condensed liquid being recycled from the phase separator in line 316 to the deethanizer column as reflux liquid therefor and the uncondensed vapor from the phase separator passing into line 317 as the recovered overhead vapor from the deethanizer column. The deethanizer column operates at approximately 280 psia (18 kg/cm$^2$), with reboil vapor being provided for the column by passage of high pressure propylene refrigerant through reboil coil 312a disposed in the bottom of the column. The deethanizer column employs a intercooler 312b in the column above the feed point. Vapor is withdrawn from the column in line 312a', at least partially condensed in the intercooler 312b by heat exchange with low pressure propylene refrigerant, and returned to the column. The deployment of the intercooler essentially transfers a portion of the condenser duty to a higher temperature and thereby reduces the energy requirement otherwise associated with condensation of the overhead from the deethanizer for reflux.

The overhead gas recovered from the deethanizer column passes in line 317 to the acetylene removal complex 326 wherein acetylene is removed from the deethanizer overhead gas to form acetylene-depleted overhead gas, discharged from the acetylene-removal complex in line 131. The acetylene-removal complex may be of various commonly known types, as for example involving washing of the overhead gas with acetone liquid for acetylene removal or, alternatively, of the catalytic hydrogenation reaction type wherein hydrogen and the overhead gas are catalytically reacted to transform the acetylene content of the gas to ethylene.

The bottoms recovered from the deethanizer column in line 318, comprising mainly $C_3$ and $C_4$ constituents, is fractionated in depropanizer column 319 to recover an overhead in line 324 comprising approximately 96% $C_3$ constituents. Overhead vapor from the depropanizer column in line 320 is cooled in heat exchanger 321 by propylene refrigerant for partial condensation therein and phase separated in phase separator 322, with the condensed liquid being recycled to the column as reflux in line 323 and the overhead gas recovered from the column in line 324 being passed to further recovery and separation steps as desired. Bottoms liquid from the depropanizer column is withdrawn therefrom in line 325, comprising mainly butadiene, and is routed to the butadiene recovery system of the ethylene plant. Reboil vapor is generated for depropanizer column 319 by passage of steam through the reboil coil 319a disposed in the lower portion of the column.

Referring now to FIG. 1B, the acetylene-depleted overhead gas in line 131, i.e., the hydrocarbon feed gas mixture for the remainder of the process, is cooled to condense a first liquid fraction comprising at least $C_1$–$C_2$ constituents and the first liquid fraction is separated from the uncondensed cooled gas. The hydrocarbon feed gas mixture in line 131 is first partially cooled in two steps in the heat exchangers 132 and 134. From line 131 the gas passes through a heat exchange passage in the heat exchanger 132 and is discharged therefrom in line 133. This gas is then cooled in heat exchanger 134 by ethylene passed through the heat exchanger in line 135. First partial cooled gas is discharged from heat exchanger 134 in line 136, containing a condensed first portion of the first liquid fraction. The first portion of the first liquid fraction is separated from the uncondensed first partial cooled gas in phase separator 137. The first portion of the first liquid fraction is withdrawn from the phase separator 137 in line 139 from which it passes through a heat exchange passage in heat exchanger 132 and is discharged into line 140. The uncondensed first partial cooled gas is withdrawn from phase separator 137 in line 138 and final partial cooled in two discreet steps. From line 138, the uncondensed gas passes through a heat exchange passage in heat exchanger 141 and is discharged therefrom in line 142 for passage through heat exchanger 143, wherein the uncondensed gas is cooled by two discreet streams of ethylene refrigerant, entering the heat exchanger in lines 148 and 149, respectively. The final partial cooled gas is discharged from heat exchanger 143 in line 144, containing a second portion of the first liquid fraction. The second portion of the first liquid fraction is separated from the uncondensed final partial cooled gas in phase separator 145. The uncondensed final partial cooled gas is discharged from the phase separator 145 in line 146. The second portion of the first liquid fraction is withdrawn from the phase separator 145 in line 147, warmed in heat exchanger 141, discharged therefrom in line 150, further warmed in heat exchanger 132, and finally discharged into line 151. The first and second portions of the first liquid fraction, in lines 140 and 151, respectively, are joined in line 152 to form the combined first liquid fraction. The first liquid fraction flows in line 152 at a flowrate of 2,918 kg-moles/hr, a pressure of 12.92 kg/cm$^2$, a temperature of $-58.9°$ C., and has the following approximate molar composition: $H_2=0.55\%$, $CH_4=21.37\%$, $C_2H_6=14.76\%$, $C_2H_4=63.28\%$ and $C_3H_6=0.02\%$. From line 152, the first liquid fraction is passed to demethanizer column 153 wherein the first liquid fraction is fractionated to recover a demethanizer overhead in line 160 comprising methane and including sigsignificant quantities of $C_2$ constituents and a demethanizer bottoms in line 164 comprising at least $C_2$ constituents. An intercooler 155 is disposed at the upper end of the demethanizer column 153 and which vapor withdrawn from the column in line 154 is cooled by ethylene refrigerant. Overhead from the demethanizer column in line 156 is cooled for partial condensation thereof in heat exchanger 157 by ethylene refrigerant and passed to phase separator 158. From phase separator 158, condensed liquid is returned to the column as reflux in line 159 and overhead vapor is recovered from the column in line 160. The recovered demethanizer overhead vapor is withdrawn in line 160 at a flowrate of 774 kg-moles/hr., a pressure of 12.64 kg/cm$^2$, a temperature of $-98.4°$ C. and with the following molar composition: $H_2=2.00\%$, $CH_4=89.36\%$ and $C_2H_4=8.64\%$. Bottoms liquid is withdrawn from the deethanizer column in line 168 and split into two portions. One portion, in line 161, is heated in heat exchanger 162 against condensed ethylene refrigerant and is returned to the column as reboiled vapor therefor. The other portion of the bottoms liquid, in line 164, is vaporized against condensing ethylene refrigerant in heat exchanger 163 and is passed through conduit 164a to a fractionation column for fractionation therein to recover ethylene as overhead product, as hereinafter described. The bottoms liquid recovered from the demethanizer column flows into line 164a at a flowrate of 2,554 kg-moles/hr, a pressure of 7.38 kg/cm$^2$, a temperature of $-53.2°$ C., and has the following molar composition: $CH_4=250$ ppm, $C_2H_6=17.46\%$, $C_2H_4=82.49\%$ and $C_3H_6=0.02\%$.

The cooled gas in line 146, from which the first liquid fraction has been separated, is warmed to substantially ambient temperature of 32° C. in heat exchangers 185 and 191. As used herein, the term "substantially ambient temperature" is broadly taken as referring to a temperature in the range of 0° to 45° C., the specific temperature in a given application depending on ambient temperature conditions. Vapor from line 146, at a flowrate of 2,895 kg-moles/hr, a pressure of 15.9 kg/cm$^2$, a temperature of $-98.4°$ C., and a molar composition of: $H_2=37.82\%$, $CO=0.02\%$, $CH_4=52.31\%$, $C_2H_6=0.52\%$ and $C_2H_4=9.33\%$, is passed through a heat exchange passage in heat exchanger 185 and discharged into line 223, further warmed in heat exchanger 191 and discharged to line 187. In heat exchanger 191, the gas is warmed against compressed feed from line 190 and cooling propylene refrigerant entering from line 224. The rewarmed gas is then compressed in compressor 188 to high superatmospheric pressure of at least 350 psia to provide warm gas at high superatmospheric pressure which is discharged into line 190. This compressed warm gas is cooled immediately downstream of the compressor by cooling water in heat exchanger 189. From line 190, the warm gas at superatmospheric pressure is further cooled in sequential steps to condense a second liquid fraction comprising $C_1$–$C_2$ constituents. The gas from line 190 enters a heat exchange passage in heat exchanger 191, is discharged into line 192, cooled in heat exchanger 185, discharged into line 193, cooled in heat exchanger 175 against low-pressure ethylene refrigerant, entering in line 174, discharged into line 194, cooled in heat exchanger 169 and discharged into line 195. These sequential cooling steps effect condensation of a second liquid fraction comprising $C_1$–$C_2$ constituents and the second liquid fraction is separated from the uncondensed further cooled gas in phase separator 196.

The further cooled gas (uncondensed vapor) is withdrawn from phase separator 196 in line 197, cooled in heat exchanger 199 against rewarming hydrogen product and low pressure methane fuel for partial condensation of the gas, such that a two-phase liquid-gas mixture is discharged from heat exchanger 199 in line 200. This two-phase mixture is phase-separated in phase separator 201. Condensed liquid is withdrawn from phase separator 201 in line 204 and throttled to lower pressure in expansion valve 205A in line 205. Separated vapor from phase separator 201 is withdrawn from the vessel in line 202. This vapor comprises approximately 95% hydrogen and 5% methane (molar composition). A portion of this hydrogen-rich vapor is withdrawn from line 202, throttled in line 203 and passed in line 205 to the phase separator 206 along with the throttled liquid underflow from phase separator 201. The liquid condensate from phase separator 206 is withdrawn in line 212 while vapor is withdrawn from phase separator 206 in line 207. The liquid and gas streams are respectively warmed in heat exchanger 199, discharged into lines 208 and 208a, warmed in heat exchanger 169, discharged into lines 209 and 209a, warmed in heat exchanger 185, discharged into lines 210 and 210a, finally warmed in heat exchanger 191 and then joined and discharged in line 211 as moderate pressure methane-rich fuel gas at a flowrate of 309 kg-moles/hr, a pressure of 3.2 kg/cm², a temperature of 32° C. and a molar composition of $H_2=28.60\%$, $CH_4=70.26\%$ and $C_2H_4=1.15\%$.

The portion of the hydrogen-rich gas in line 202 which is not diverted into line 203 passes in line 213 to heat exchanger 199 for warming therein. The warm hydrogen-rich gas is discharged from heat exchanger 199 in line 214 and split into two portions with one portion being passed into line 215 and throttled and the remainder passing in line 216 to the heat exchanger 169 for additional warming therein. Additionally warmed hydrogen-rich gas is discharged from heat exchanger 169 in line 217, warmed in heat exchanger 185, discharged into line 218, finally warmed in heat exchanger 191 and discharged in line 219 from the process as hydrogen product gas, at a flow rate of 808 kg-moles/hr, a pressure of 33.74 kg/cm², a temperature of 32° C. and with aforementioned molar composition of approximately 95% hydrogen and 5% methane.

The second liquid fraction withdrawn from phase separator 196 in line 198 is throttled to low superatmospheric pressure below 200 psia in expansion valve 198A. The throttled second liquid fraction is then mixed with the overhead gas recovered from the demethanizer column in line 160 after the latter has been partially cooled in heat exchanger 169. The combined stream forms a fluid mixture comprising $C_1$–$C_2$ constituents in line 170. This stream is introduced from line 170 into a stripping zone 171 wherein $C_1$ constituents are stripped from the fluid mixture by methane-containing vapor, entering the stripping zone in line 180, to recover a methane-rich vapor overhead in line 172 and bottoms liquid containing $C_2$ constituents in line 173. The methane-rich overhead recovered from the stripping zone in line 172 is warmed in heat exchanger 169, discharged in line 220, warmed in heat exchanger 185, discharged in line 221, warmed in heat exchanger 191, and discharged from the process in line 222 at a flow rate of 2,142 kg-moles/hr, a pressure of 3.2 kg/cm², a temperature of 32° C. and with the following approximate molar composition: $H_2=11.90\%$, $CH_4=87.79\%$ and $C_2H_4=0.27\%$.

The bottoms liquid recovered from the stripping zone in line 173 is joined with the aforementioned hydrogen-rich stream in line 215, and the combined stream flows in line 176 to heat exchanger 169 for partial vaporization of the stripping zones bottoms liquid therein to form a fluid mixture comprising methane-containing vapor. The resulting vapor-liquid mixture flows in line 177 and is joined by throttled pressurized liquid from line 183, to be described more fully hereinafter, to form the combined stream in line 178 which is passed to phase separator 179. From phase separator 179, the vaporized methane-containing vapor is withdrawn in line 180 and recycled to the stripping zone as aforementioned methane-containing vapor therefor.

Unvaporized stripping zone bottoms liquid is withdrawn from the phase separator 179 in line 181, pressurized in pressurizing pump 182 and then divided, with a portion of the pressurized liquid being throttled and then recycled in line 183 for joining with the stripping zone bottoms liquid in line 177, as previously described. The remaining portion of the pressurized unvaporized stripping zone bottoms liquid is passed in line 184 to heat exchanger 185 for partial warming thereof and is discharged in line 186 and passed to the demethanizer column 153 for fractionation therein with the first liquid fraction, entering the column in line 152.

Referring now to FIG. 1c, demethanizer bottoms in line 164a, at a flow rate of 2,554 kg-moles/hr, a pressure of 7.38 kg/cm², a temperature of −53.2° C., and with a molar composition of $C_2H_6=17.46\%$, $C_2H_4=82.49\%$ and $C_3H_6=0.2\%$, enters the base of the fractionation column 225. The fractionation column 225 comprises a first rectification zone 226, a second rectification zone 229 having a lower end 228 in direct heat transfer communication with an upper end 227 of the first rectification zone 226, and a third rectification zone 232 having a lower end 231 in direct heat transfer communication with an upper end 230 of the second rectification zone 229. The first and second rectification zones are in direct heat transfer communication via a reboil coil 234 which extends from the upper end 227 of the first rectification zone 226, passes through the lower end 228 of second rectification zone of 229 and discharges in the upper end 227 of first rectification zone of 226 on liquid receiving pan 235, from which liquid overhead is withdrawn from the first rectification zone in line 236. The second rectification zone is in direct heat transfer communication with third rectification zone 232 via reboil coil 242 which passes from the upper end 230 of second rectification zone of 229, is disposed in the lower end 231 of third rectification zone 232, and discharges in the upper end 230 of second rectification zone 229 onto receiving pan 243 from which liquid overhead is withdrawn from the second rectification zone 229 in line 244.

In the first rectification zone, the vaporized demethanizer column bottoms, entering the zone from line 164, are rectified to recover ethylene-rich overhead in line 236 and ethane-rich bottoms in line 251. The ethane-rich bottoms from the first rectification zone are throttled in valve 252 to lower superatmospheric pressure and fed to an intermediate portion of the second rectification zone 229. In the second rectification zone, the throttled ethane-rich bottoms recovered from the first rectification zone is rectified to recover ethylene-rich overhead in line 244 and ethane-rich bottoms in line 253. The ethane-rich bottoms recovered from the second rectification zone in line 253 is throttled to still lower atmospheric pressure in valve 254 and fed to an intermediate portion of the third rectification zone 232. In the third rectification zone, the throttled ethane-rich bottoms recovered from the second rectification zone is rectified to recover ethylene overhead in line 248 and ethane bottoms in line 255. The ethane bottoms from rectification zone 232 in line 255 are cooled by ethylene refrigerant in heat exchanger 256 and discharged from the process at a flow rate of 453 kg-moles/hr, a pressure of 6.38 kg/cm$^2$, a temperature of 32° C., and with the following approximate molar composition: $C_2H_6$=98.14%, $C_2H_4$=1.74% and $C_3H_6$=0.11%.

The ethylene-rich overhead recovered from the first rectification in line 236 is cooled in heat exchanger 237, discharged into line 238, throttled to still lower superatmospheric pressure in valve 239, cooled in heat exchanger 240 and discharged into line 241. The ethylene-rich overhead recovered from the second rectification zone in line 244 is cooled in heat exchange 240, discharged into line 245, throttled to the still lower superatmospheric pressure in valve 246 and combined with the ethylene-rich overhead recovered from the first rectification zone, which has been cooled and throttled to the still lower superatmospheric pressure, from line 241 and the combined stream is passed in line 247 to the upper end 233 of the third rectification zone 232 as reflux to enhance the rectification therein. The ethylene overhead recovered from the rectification zone in line 248 is partially warmed in the exchanger 240, discharged into line 249, further warmed in exchanger 237 and discharged from the process in line 250 at a flow rate of 2,101 kg-moles/hr, a pressure of 0.73 kg/cm$^2$, a temperature of −69.2° C., and with a molar composition of $CH_4$=0.03%, $C_2H_6$=0.07%, and $C_2H_4$=99.9%. This ethylene product stream may then be passed to ethylene product compressors for raising the pressure of the product gas to a suitable level for disposition and/or other end use and also to raise its temperature to substantially ambient level.

As shown by the foregoing description, the FIG. 1 embodiment of the present invention is able to operate with various recovery and separation steps at pressure levels on the order of 100 to 350 psia, with the use of only ethylene and propylene as refrigerant fluids. As a result, this embodiment of the present invention permits a substantial power savings to be realized relative to the compression energy requirements of prior art ethylene separation processes.

In the embodiment of this invention described above in connection with FIG. 1, the hydrocarbon feed gas mixture introduced to the first liquid fraction condensation cooling step is provided at a pressure of between 200 and 350 psia. Hydrocarbon feed gas mixture pressures below 200 psia are not desirably employed inasmuch as such lower pressure would necessitate the use of additional refrigeration, beyond that available with only ethylene-propylene refrigeration, in order to achieve satisfactory separations in the successive fractionation steps. On the other hand, hydrocarbon feed gas mixture pressures above 350 psia are generally undesirable in this embodiment for the reason that at such high pressures the relative volatilities of the hydrocarbon mixture constituents are excessively decreased relative to the requirements for efficient fractionation separation.

In the process step of cooling the hydrocarbon feed gas mixture to condense a first liquid fraction, the hydrocarbon feed gas mixture is desirably cooled to a temperature below about −93° C. (180° K.) in order to condense sufficient $C_2$ constituents so as to carry out the subsequent demethanizer column fractionation of the first liquid fraction at suitably low pressure levels. In this respect, the demethanizer column fractionation is desirably conducted at pressure below about 350 psia, so as to minimize the amount of ethylene refrigeration (and hence refrigeration compression) necessary to condense reflux for the demethanizer column. In addition, the demethanizer column fractionation is desirably conducted at at least 100 psia so as to accommodate refrigeration temperature levels available with the use of only ethylene-propylene refrigeration.

In the broad practice of the process as described in connection with FIG. 1, the cooled overhead gas from which the first liquid fraction has been separated is warmed to substantially ambient (atmospheric) temperature and compressed to high superatmospheric pressure of at least 350 psia, as for example 350 to 450 psia, to provide warm overhead gas at high super-atmospheric pressure. Pressures below 350 psia are to be avoided in this compression step since they unduly increase the difficulty of the subsequent cooling and phase separation steps to which the warm overhead gas at high superatmospheric pressure is subjected, by increasing the external refrigeration requirements associated therewith. In these subsequent cooling and phase separation steps, a second liquid fraction is condensed and separated and thereafter throttled to low superatmospheric pressure below 200 psia, as for example from 50 to 200 psia. Throttling to pressures above 200 psia is to be avoided since such involves the loss of substantial potential self-refrigeration in the throttling process by Joule-Thompson inversion cooling.

The advantages of the above-described embodiment of the present invention relative to prior art processes will be shown more fully by the examples set forth herein below. (Note: The metric pressures in the preceding description of a preferred embodiment of this invention are gauge pressures, while the metric pressures in Examples I and II below are absolute pressures.)

EXAMPLE I

This Example is based on a conventional prior art ethylene separation process utilizing a so-called 'front-end' depropanizer column.

In this prior art process, a ligh naphtha feedstock, of the composition described above in connection with the preferred embodiment of the instant invention, is cracked by pyrolysis and subjected to water removal and gasoline fractionation operations to yield a hydrocarbon gas mixture. The hydrocarbon gas mixture is compressed to high pressure of approximately 540 psia (38 kg/cm$^2$) and fractionated in a depropanizer column to recover a $C_3$ and lighter overhead and $C_4$ and heavier bottoms.

The $C_3$ and lighter overhead stream from the depropanizer column, containing ethylene, passes respectively through forecoolers which utilize high and low pressure propylene refrigeration, and then passes to a first forecooling stripper. In the first forecooling stripper, a liquid fraction of substantially $C_2$'s and $C_3$'s is separated and fed to a pre-fractionation column, and a vapor fraction is separated and passed to a second forecooling stripper. Reflux for the first forecooling stripper is provided by high pressure ethylene refrigeration. In addition to the vapor stream from the first forecooling stripper, the overhead recovered from the prefractionation column, which comprises primarily $CH_4$ and $C_2H_4$, is also passed to the second forecooling stripper. The bottoms of the second forecooling stripper, consisting primarily of $CH_4$ and $C_2$'s are passed to a demethanizer column, while the overhead is passed to a cold box complex. Reflux for the second forecooling stripper is provided by low pressure ethylene refrigeration.

The cold box complex is provided with various heat exchangers, phase separators, and the requisite piping and valving. In the cold box complex a number of heat exchange and phase separation steps are performed to yield a low and a high pressure fuel gas stream comprising primarily $CH_4$, as well as a product hydrogen stream, in a manner well-known to one of ordinary skill in the art.

The prefractionation column, whose feed comprises the bottoms of the first forecooling stripper, produces a bottoms stream consisting of primarily $C_2$'s and $C_3$'s. This stream subsequently forms the sole feed for a deethanizer column. The overheads of the prefractionation column are cooled against low pressure propylene in a condenser, and are fed to a phase separator. The vapor fraction from the phase separator (recovered overhead) passes to a booster compressor and then forms part of the feed for the second forecooling stripper. The bottoms from the phase separator are split; one portion provides reflux for the prefractionation column while the remainder is sent as feed to the demethanizer column.

The demethanizer column produces an overhead of 94% $CH_4$. This stream passes to the cold box complex for refrigeration recovery and subsequently forms high pressure fuel for the process. Bottoms from the demethanizer column form one portion of the feed for the ethylene ($C_2$ separation) column.

The deethanizer column receives feed from the prefractionation column and produces a bottoms stream containing predominately $C_3$'s, from which propylene is subsequently recovered in a propylene column, and an overhead stream containing $C_2H_4$ and $C_2H_6$, which is fed to the ethylene column. Reflux for the deethanizer column is provided by low pressure propylene. The ethylene column operates at approximately 300 psia (21 kg/cm$^2$) and separates a combined feed stream from the demethanizer column and the deethanizer column into an overhead stream of 98.4% $C_2H_4$ and 1.5% $C_2H_2$ at 300 psia (21 kg/cm$^2$) and $-18°$ F. ($-28°$ C.) and bottoms stream of 97.4% $C_2H_6$ and 2% $C_2H_2$ at 370 psia (26 kg/cm$^2$) and $-30°$ F. ($-34°$ C.). Reflux for the ethylene column is provided by low pressure propylene, while boilup is provided by medium pressure propylene. The overhead ethylene stream is passed to an acetylene removal section where acetylene is removed by an acetone wash. A 99.9% ethylene product is recovered overhead. The ethane bottoms from the ethylene column are recycled to the pyrolysis furnaces.

In this type of olefins plant, refrigeration is normally supplied by ethylene and propylene at temperature levels down to about $-100°$ C. The details of these refrigeration systems are well-known and as such, require only brief summary here.

In the propylene system, two levels of refrigeration are provided. Propylene vapors enter the suction of a propylene refrigeration compressor and are compressed to a high pressure, for example 240 psia (16.8 kg/cm$^2$). Portions of the compressor discharge are condensed and cooled by heat exchange with process streams (e.g., prefractionation column reboiler, demethanizer column reboiler and ethylene column reboiler), while another portion is condensed against chilled water. One portion of the condensed liquid then flows to a first flash tank. A portion of the liquid from this flask tank flows to various process heat exchangers providing refrigeration at the medium pressure level, and passes to a second flask tank. Liquid from the second flask tank flows to process heat exchangers and provides the lower temperature refrigeration. The vapors from the process heat exchangers and the flask tanks are returned to the propylene refrigeration compressor.

In the ethylene refrigeration system, two refrigeration levels are generally supplied. The workings of the ethylene system are similar to those of the propylene system, with the high pressure ethylene compressor discharge being condensed by heat exchange with propylene refrigerant.

The major compression requirements for the high pressure ethylene separation process, producing 1000 MM lbs/year of ethylene, are tabulated in Table I below. The total compression requirement is approximately 86,039 brake horsepower (bhp). This requirement can be reduced by about 5000 to 6000 hp by increasing the number of propylene compressors to more closely comply with user levels, however, the compexity is attendantly increased.

TABLE I

COMPRESSION REQUIREMENTS FOR THE CONVENTIONAL HIGH PRESSURE ETHYLENE PROCESS

| | | |
|---|---|---|
| Furnace Gas Compression | | 38,811 bhp |
| Propylene Refrigeration | | 38,890 bhp |
| Ethylene Refrigeration | | 7,338 bhp |
| | Total | 86,039 bhp |

EXAMPLE II

It is known in the art to employ a so-called "triple column" for fractionation of an ethane-ethylene $C_2$ mixture in the ethylene process to recover ethylene as overhead product and ethane as bottoms product. The triple column comprises three consecutively arranged rectification zones coupled in direct heat transfer contact such that the lower end of the second rectification zone is in direct heat transfer communication with the upper end of the first rectification zone and the lower end of the third rectification zone is in direct heat transfer communication with the upper end of the second rectification zone. In the triple column, overheads from the first and second rectification zones are throttled and introduced to an upper part of the third rectification zone. Bottoms from the first rectification zone are introduced as feed to the second rectification zone and bottoms from the second rectification zone are introduced as feed to the third rectification zone. Bottoms from the third rectification zone are recovered as ethane product and ethylene product is recovered as overhead therefrom.

Due to the low operating pressure of the triple column, relative to the conventional ethylene column employed in the Example I process (the first rectification zone of the triple column can typically operate below 100 psia), the triple column may suitably be employed in a low pressure ethylene separation process.

This Example is based on a low pressure ethylene separation process utilizing an ethylene separation triple column wherein the hydrocarbon gas mixture from the pyrolysis furnace (operating on the same light naphtha feedstock as the Example I high pressure process) and the water removal and gasoline fractionation steps is compressed to a pressure on the order of 140 psia (8.4 kg/cm$^2$). The compressed hydrocarbon gas mixture is then passed to a $C_4/C_5$ splitter column to recover overhead comprising $C_4$ and lighter constituents and bottoms comprising $C_5$ and heavier constituents. The recovered overhead from the $C_4/C_5$ splitter column is then passed to a deethanizer column wherein $C_2$'s and lighter are separated from $C_3$'s and heavier. The overhead stream recovered from the deethanizer column has a temperature of 101° F. (−74° C.), a pressure of 120 psia (kg/cm$^2$) and the following approximate molar composition: $H_2$=19.5%, CO=0.04%, $CH_4$=36.6%, $C_2H_2$=0.53%, $C_2H_4$=35.7%, $C_2H_6$=7.6% and $C_3H_6$=0.01%.

In the process of this Example, acetylene is removed prior to further processing of the $C_2$ and lighter stream. Acetylene can be removed by solvent absorption or by catalytic hydrogenation. Acetylene removal at this point of the treatment sequence provides some saving in total refrigeration requirements of later treatment steps.

The $C_2$'s and lighter stream from which acetylene has been removed, then passes to a demethanizer column operating at about 100 psia (7.0 kg/cm$^2$). The demethanizer column produces a bottoms of 82% $C_2H_4$ and 18% $C_2H_6$ which is fed to the triple column, and an overhead of 26% $H_2$, 62% $CH_4$, and 12% $C_2H_4$.

The overhead from the demethanizer column is warmed to substantially ambient temperature and is then compressed to about 400 psia. This compressed gas mixture is then cooled in various heat exchangers against cold box products and ethylene refrigeration to produce a first liquid fraction. This first liquid fraction is recovered in a phase separator and provides reflux for the demethanizer column, while the vapor fraction recovered from the phase separator is further cooled and then passed to a second phase separator.

The vapor and liquid fractions recovered from the second phase separator are then subjected to heat exchange and phase separation operations in a cold box of conventional design to yield at high pressure hydrogen product at pressure of 464 psia (32.5 kg/cm$^2$) with a molar composition of 95% $H_2$ and 5% $CH_4$, a first low pressure fuel gas stream at a pressure of 65 psia (4.5 kg/cm$^2$) with a molar composition of 45% $H_2$ and 55% $CH_4$, and a second low pressure fuel gas stream at a pressure of 66 psia (4.5 kg/cm$^2$) with a molar composition of 95% $CH_4$ and 5% $H_2$. The triple column produces an overhead ethylene product of 99.5% $C_2H_4$ at 20 psia (1.4 kg/cm$^2$) and −141° F. (−96° C.) and a bottoms ethane stream of 98% $C_2H_6$ and 2% $C_2H_4$ at 24 psia (1.7 kg/cm$^2$) and −112° F. (−80° C.).

The major compression requirements for this process are tabulated in Table II below. The total compression requirement is approximately 85,665 bhp, using conventional ethylene and propylene refrigeration.

TABLE II

| COMPRESSION REQUIREMENTS FOR THE LOW PRESSURE ETHYLENE PROCESS | |
|---|---|
| Furnace Gas Compression | 34,772 bhp |
| Propylene Refrigeration | 28,055 bhp |
| Ethylene Refrigeration | 22,838 bhp |
| | 85,665 bhp |

EXAMPLE III

This Example is based on a moderate pressure process according to this invention, operating on the same light naphtha feedstock as the processes of Example I and II and operating as shown and described in connection with FIGS. 1a, 1b and 1c herein.

The compression requirements for this Example are tabulated in Table III below.

TABLE III

| COMPRESSION REQUIREMENTS FOR THE MODERATE PRESSURE PROCESS OF THIS INVENTION | | |
|---|---|---|
| Furnace Gas Compression | | 32,685 bhp |
| Propylene Refrigeration | | 10,110 bhp |
| Ethylene Refrigeration | | 18,350 bhp |
| $C_2H_4$ Product Compression | | 5,440 bhp |
| | Total | 66,585 bhp |

The total power requirement of 66,585 bhp for this invention represents a 22% power savings relative to the conventional high pressure process, and a 19% savings relative to the conventional low pressure process utilizing a triple column.

Figure 2:
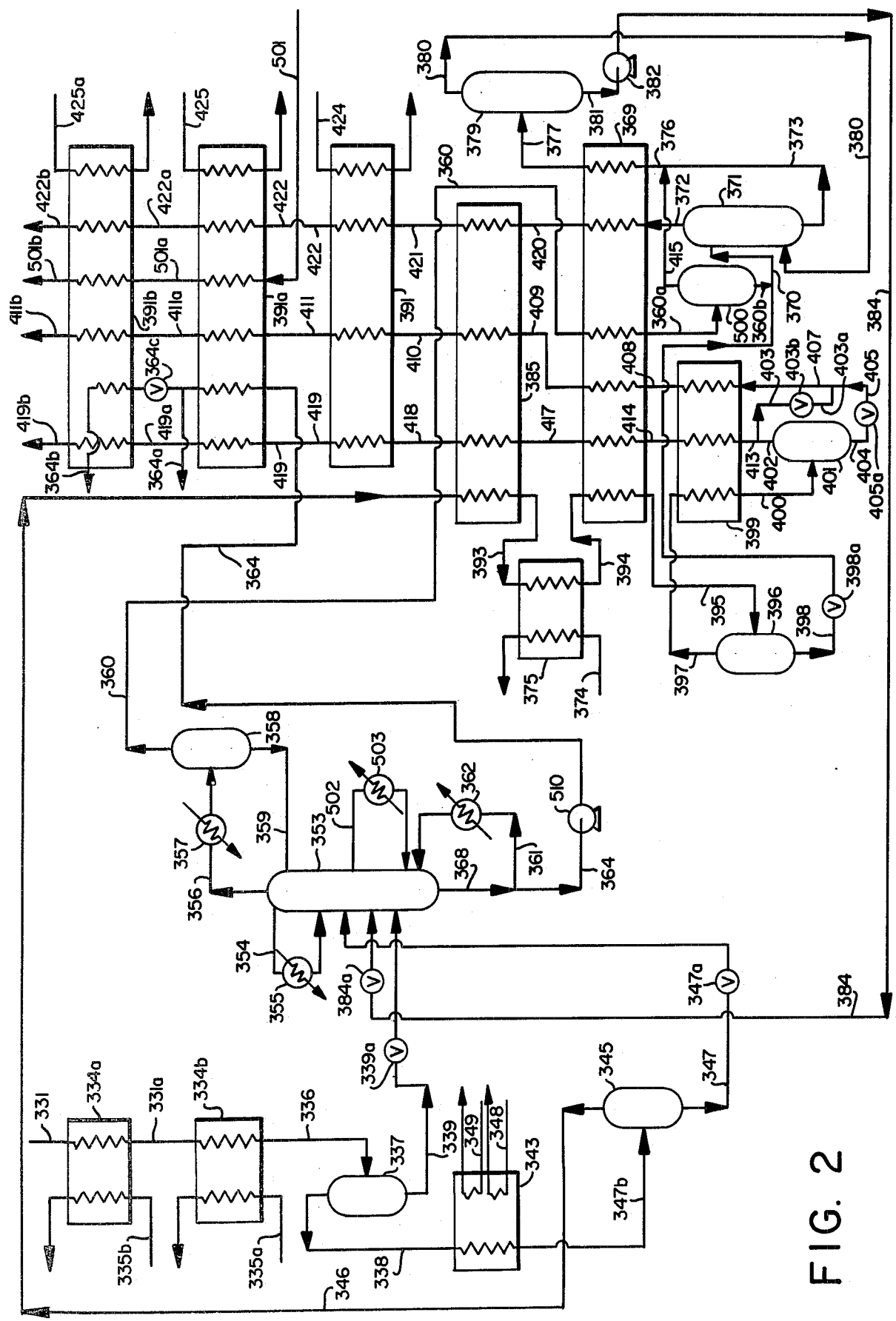
FIG. 2 is a flow sheet embodying another process according to the present invention.

FIG. 2 is a flow sheet embodying another process according to the present invention, such as may be advantageously implements in a conventional high pressure ethylene separation plant. Hydrocarbon feed gas mixture enters the process in line 331 at a flow rate of 5238 kg-moles/hr., a pressure of 33.36 kg/cm$^2$ (474.5 psia), a temperature of −10° C. and with the following approximate molar composition: $H_2$=14.60%, $CH_4$=31.00%, $C_2H_2$=0.43%, $C_2H_6$=5.07%, $C_2H_4$=32.68%, $C_3$'s=12.18% and $C_4$'s=3.66%. This feed gas mixture constitutes the remaining constituents of a hydrocarbon gas mixture which has previously been subjected to pyrolytic cracking, water quench, gasoline fractionation, acid gas removal and compression steps, all carried out in a conventional high pressure ethylene plant.

The hydrocarbon feed gas mixture entering the process in line 131 is sequentially cooled in heat exchangers 334a and 334b by propylene refrigerant passed through the heat exchangers in lines 335a and 335b, respectively. The hydrocarbon feed gas mixture discharged from heat exchanger 334a in line 331a can be additionally cooled, if desired, by heat exchange in heat exchanger 362 with the bottoms liquid recovered from demethanizer column 353, to be described more fully hereinafter. First partial cooled hydrocarbon feed gas mixture is discharged from heat exchanger 334b in line 336, containing a condensed first portion of a first liquid fraction. The first portion of the first liquid fraction is separated from the uncondensed first partial cooled gas in phase separator 337 and passed in line 339 through throttle valve 339a to demethanizer column 353.

The uncondensed first partial cooled gas is withdrawn from phase separator 337 in line 338 and final partial cooled in heat exchanger 343 by two discreet streams of ethylene refrigerant flowing through the heat exchanger in lines 348 and 349, respectively. The final partial cooled gas is discharged from heat exchanger 343 in line 347, containing a second portion of the first liquid fraction. The second portion of the first liquid fraction is separated from the uncondensed final partial cooled gas in phase separator 345, with the latter being discharged from the phase separator 345 in line 346. The second portion of the first liquid fraction is withdrawn from the phase separator 345 in line 347 from which it passes through throttle valve 347a to the demethanizer column 353. The first portion of the first liquid fraction in line 339 has a flowrate of 2,238 kg-moles/hr., a pressure before throttling in valve 339a of 33.36 kg/cm$^2$ (474.5 psia), a temperature of $-35°$ C., and the following approximate molar composition: $H_2=0.87\%$, $CH_4=14.16\%$, $C_2H_2=0.55\%$, $C_2H_6=7.11\%$, $C_2H_4=42.49\%$, $C_3$'s$=26.05\%$ and $C_4$'s$=8.36\%$. The second portion of the first liquid fraction in line 347 has a flow rate of 844 kg-moles/hr., a pressure before throttling in valve 347a of 33.36 kg/cm$^2$ (474.5 psia), a temperature of $-70.4°$ C., and the following approximate molar composition: $H_2=1.19\%$, $CH_4=29.06\%$, $C_2H_2=0.81\%$, $C_2H_6=8.81\%$, $C_2H_4=53.13\%$, $C_3$'s$=6.29\%$ and $C_4$'s$=0.57\%$. In lines 339 and 347, the first and second portions of the first liquid fraction are trottled in valves 339a and 347a, respectively, to the 150 psia pressure operating level of the demethanizer column 353.

In the demethanizer column 353, the first liquid fraction is fractionated to recover a demethanizer overhead in line 360 comprising methane and a demethanizer bottoms in line 364 comprising at least C$_2$ constituents. An intercooler 355 is disposed at the upper end of the demethanizer column 353 in which vapor withdrawn from the column in line 354 is cooled by ethylene refrigerant, and another interstage heat exchanger 503 is disposed at the lower end of the demethanizer column 353 in which liquid withdrawn from the column in line 502 is heated as for example by heat exchange with the hydrocarbon feed gas mixture for additional cooling of the latter. Overhead vapor from the demethanizer column in line 356 is cooled for partial condensation thereof in heat exchanger 357 by ethylene refrigerant and is passed to phase separator 358. From phase separator 358, condensed liquid is returned to the column as reflux in line 359 and recovered overhead vapor from the column is withdrawn from phase separator 358 in line 360. The recovered demethanizer overhead vapor in line 360 has a flowrate of 784 kg-moles/hr., a pressure of 10.02 kg/cm$^2$ (142.5 psia), a temperature of $-96.5°$ C., and the following molar composition: $H_2=3.78\%$, $CH_4=83.88\%$, $C_2H_2=0.14\%$, $C_2H_6=0.56\%$, and $C_2H_4=11.40\%$.

Bottoms liquid is withdrawn from the demethanizer column in line 368 and split into two portions. One portion passes in line 361 to heat exchanger 362 for heating therein by heat exchange as for example with hydrocarbon feed gas mixture in line 331a for cooling thereof. In heat exchanger 362, bottoms liquid is revaporized and the resulting reboil vapor is returned to column 353 in line 361. The remainder of the bottoms liquid is recovered from the column in line 364 and pumped to higher pressure in pump 510 therein. The recovered bottoms liquid discharged from pump 510 has a flowrate fo 2848 kg-moles/hr., a pressure of 27.42 kg/cm$^2$ (390.0 psia), a temperature of $-35°$ C. and the following molar composition: $CH_4=0.250\%$, $C_2H_2=0.76\%$, $C_2H_6=9.38\%$, $C_2H_4=60.00\%$, $C_3$'s$=22.56\%$ and $C_4$'s$=6.80\%$. The pressurized bottoms liquid discharged from pump 510 flows in line 364 through heat exchanger 391a for heat exchange therein with cooling propylene refrigerant flowing through the heat exchanger in line 425. The demethanizer bottoms discharged from heat exchanger 391a is then divided, with one portion being withdrawn in line 364a and the remainder passing through valve 346c, then passed through heat exchanger 391b against cooling propylene refrigerant flowing through the heat exchanger in line 425a, and finally withdrawn in line 364b. The demethanizer bottoms streams in lines 364a and 364b are passed to a deethanizer column (not shown) for recovery of C$_2$ overhead, which is then fractionated in a C$_2$ fractionation column (not shown) to recover ethylene as overhead product and ethane bottoms.

The uncondensed cooled gas in line 346, from which the first liquid fraction has been separated, is passed at a flowrate of 2,160 kg-moles/hr., a pressure of 33.36 kg/cm$^2$ (474.5 psia), a temperature of $-70.4°$ C., and a molar composition of: $H_2=34.0\%$, $CO=0.46\%$, $CH_4=49.16\%$, $C_2H_6=1.51\%$, and $C_2H_4=14.54\%$, through a heat exchange passage in heat exchanger 385 and discharged into line 393. From line 393 this gas is further cooled in heat exchanger 375, against low-pressure ethylene refrigerant flowing through the heat exchanger in line 374, and is then discharged into line 394, still further cooled in heat exchanger 369 and finally discharged into line 395. These sequential cooling steps effect condensation of a second liquid fraction comprising $C_1$-$C_2$ constituents. The second liquid fraction is separated from the uncondensed further cooled gas in phase separator 396.

The uncondensed further cooled gas separated in phase separator 396 is withdrawn therefrom in line 397 and cooled in heat exchanger 399, against rewarming hydrogen product from line 413 and low pressure methane fuel from line 407, for partial condensation thereof, with the resulting two-phase vapor-liquid mixture being discharged from heat exchanger 399 in line 400. This two-phase mixture is then phase-separated in phase separator 401. Condensed liquid is withdrawn from phase separator 401 in line 404 and throttled to lower pressure in expansion valve 405a in line 405. Uncondensed vapor is removed from phase separator 401 in line 402. This vapor has a molar composition of approximately 95% hydrogen and 5% methane. A portion of this hydrogen-rich vapor is withdrawn from line 402 in line 403, throttled to lower pressure in valve 403b and passed to line 405 through line 403a. In line 405 the throttled vapor is joined with the throttled liquid underflow from phase separator 401 to form the two-phase stream in line 407. From line 407 this stream is warmed in heat exchanger 399, discharged into line 408, warmed in heat exchanger 369, discharged into line 409, warmed in heat exchanger 385, discharged into line 410, warmed in heat exchanger 391 against subcooling ethylene from line 424, discharged into line 411, warmed in heat exchanger 391a against subcooling propylene from line 425, discharged into line 411a, finally warmed in heat exchanger 391b against subcooling propylene in line 425a and discharged in line 411b as low pressure methane-rich fuel gas at a flowrate of 284 kg-moles/hr., a pressure of 1.48 kg/cm$^2$ (21.1 psia), a temperature of 32° C. and with a molar composition of $H_2 = 5.0\%$, $CH_4 = 92.3\%$, $CO = 1.0\%$ and $C_2H_2 = 1.64\%$.

The portion of the hydrogen-rich gas in line 402 which is not diverted into line 403 flows in line 413 through heat exchanger 399 for warming therein. Warm hydrogen-rich gas is discharged from heat exchanger 399 into line 414 and passed to heat exchanger 369 for additional warming therein. Additionally warmed hydrogen-rich gas is discharged from heat exchanger 369 into line 417, warmed in heat exchanger 385, discharged into line 481, warmed in heat exchanger 391, discharged into line 419, warmed in heat exchanger 391a, discharged into line 419a, finally warmed in heat exchanger 391b, and discharged from the process in line 419b as product hydrogen gas, at a flow rate of 716 kg-moles/hr., a pressure of 33.36 kg/cm$^2$ (474.5 psia), a temperature of 32° C. and with the aforementioned molar composition of approximately 95% hydrogen and 5% methane.

The second liquid fraction withdrawn from phase separator 396 in line 398 is throttled to low superatmospheric pressure below 200 psia in expansion valve 398a. The throttled second liquid fraction is then mixed with demethanizer overhead liquid recovered from the separator 500 wherein demethanizer overhead vapor from line 360 is separated after cooling for partial condensation thereof in heat exchanger 369. The combined stream of throttled second liquid fraction and demethanizer overhead liquid in line 370 forms a fluid mixture comprising $C_1$–$C_2$ constituents. This stream is introduced from line 370 into a stripping zone 371 wherein $C_1$ constituents are stripped from the fluid mixture by methane-containing vapor, introduced to the stripping zone from line 380, to recover a methane-rich vapor overhead in line 372 and bottoms liquid containing methane and $C_2$ constituents in line 373. The methane-rich overhead recovered from the stripping zone in line 372 is warmed in heat exchanger 369, discharged into line 420, warmed in heat exchanger 385, discharged into line 421, warmed in heat exchanger 391, discharged into line 422, warmed in heat exchanger 391a, discharged into line 422a, warmed in heat exchanger 391b and discharged from the process in line 422b at a flow rate of 1426 kg-moles/hr., a pressure of 4.2 kg/cm$^2$ (59.7 psia), a temperature of 32° C. and with the following approximate molar composition: $H_2 = 3.7\%$, $CO = 0.32\%$, $CH_4 = 95.41\%$ and $C_2H_4 = 0.59\%$.

The bottoms liquid recovered from the stripping zone 371 in line 373 is joined with the overhead stream from separator 500 in line 415, and the combined stream flows in line 376 to heat exchanger 369 for partial vaporization of the stripping zone bottoms liquid therein to form a fluid mixture comprising methane-containing vapor. This vapor-liquid fluid mixture flows in line 377 to phase separator 379 for separation therein of methane-containing vapor from the unvaporized stripping zone bottoms liquid. From phase separator 379, the vaporized methane-containing vapor is withdrawn in line 380 and passed to the stripping zone as the aforementioned methane-containing vapor therefor. The unvaporized stripping zone bottoms liquid is withdrawn from the phase separator 379 in line 381, pressurized in pump 382 and passed in line 384 having throttle valve 384a therein to the demethanizer column 353 for fractionation therein with the first and second portions of the first liquid fraction, entering the column in lines 339 and 347, respectively.

In the general practice of the embodiment of the invention corresponding to that described above in connection with FIG. 2, hydrocarbon feed gas mixture is provided to the process at superatmospheric pressure between 200 and 700 psia. Such pressure range includes the pressure levels characteristic of conventional high pressure ethylene plants, e.g., 500–700 psia, reflecting the applicability of this embodiment of the invention as a "retrofitted" design modification of high pressure plants to increase operating economy thereof. Such improvement derives in part from carrying out demethanization at moderate pressure in the recovery section of the ethylene plant, thereby permitting a substantial refrigeration system power savings to be realized relative to the refrigeration system compression energy requirements of conventional high pressure ethylene separation processes wherein demethanization is carried out at high pressures as for example 500 psia.

In the embodiment of this invention described above in connection with FIG. 2, the hydrogen feed gas mixture introduced to the first liquid fraction condensation cooling step is provided at a pressure of between 350–700 psia. Hydrocarbon feed gas mixture pressures of 350 psia and above are typical of gas mixture streams provided after preliminary compression and separation steps have been carried out in conventional high pressure ethylene separation plants. The upper limit of hydrocarbon feed gas mixture pressure of 700 psia represents the approximate upper operating pressure level characteristic of conventional high pressure ethylene plants, to which the process embodiment of FIG. 2 may advantageously be applied.

Subsequently, in this embodiment, the first liquid fraction separated from the cooled hydrocarbon feed gas mixture is fractionated in a demethanizer column at superatmospheric pressure of 100 to 350 psia. The demethanization pressure level is at least 100 psia for the reason that at lower pressures, correspondingly lower temperature refrigeration is required for reflux condensation, such as cannot be accommodated by ethylene-propylene refrigeration alone. As discussed earlier herein, lower temperature refrigeration below the levels provided by ethylene-propylene refrigeration generally requires the use of methane refrigerant. Methane refrigeration in turn increases the overall compression requirements for refrigeration in the ethylene plant. By contrast, an objective of the present invention is to reduce the refrigeration compression requirement of the ethylene separation process relative to conventionally employed processes. For this reason the demethanization pressure level should be at least 100 psia. On the other hand, the demethanizer column fractionation step is desirably conducted at pressure below about 350 psia, so as to minimize the amount of ethylene refrigeration (and hence refrigeration compression) necessary to condense reflux for the demethanizer column.

Also, in the broad practice of the embodiment of this invention described above in connection with FIG. 2, the uncondensed gas from which the first liquid fraction has been separated is further cooled at high superatmospheric pressure of at least 350 psia to condense a second liquid fraction. Pressures below 350 psia are to be avoided in this step since they unduly increase the difficulty of the cooling and phase separation steps to which the uncondensed gas is subjected, by increasing the external refrigeration requirements associated therewith. Subsequently, the second liquid fraction is separated from the uncondensed further cooled gas and thereafter throttled to low superatmospheric pressure below 200 psia, as for example from 50 to 200 psia. Throttling to pressures above 200 psia is to be avoided since such involves the loss of substantial potential self-refrigeration in the throttling process by Joule-Thompson inversion cooling.

Although preferred embodiments have been described in detail, it will be further appreciated that other embodiments are contemplated only with modification of the disclosed features, as being within the scope of the invention.

What is claimed is:

1. A process for separating a hydrocarbon feed gas mixture comprising at least $C_1$–$C_2$ constituents including ethylene to produce a separated ethylene product, comprising the steps of:
   (a) providing said hydrocarbon feed gas mixture at superatmospheric pressure between 200 and 700 psia, cooling same to condense a first liquid fraction comprising at least $C_1$–$C_2$ constituents, and separating said first liquid fraction from the uncondensed gas;
   (b) fractionating the first liquid fraction in a demethanizer column at superatmospheric pressure of 100 to 350 psia to recover a demethanizer overhead comprising methane and a demethanizer bottoms comprising at least $C_2$ constituents;
   (c) fractionating the demethanizer bottoms to recover ethylene as overhead product and ethane bottoms;
   (d) further cooling the uncondensed gas of step (a) at high superatmospheric pressure of at least 350 psia to condense a second liquid fraction comprising $C_1$–$C_2$ constituents, and separating the second liquid fraction from the uncondensed further cooled gas;
   (e) throttling the second liquid fraction to low superatmospheric pressure below 200 psia;
   (f) mixing the throttled second liquid fraction with the demethanizer overhead to form a fluid mixture comprising $C_1$–$C_2$ constituents;
   (g) stripping $C_1$ constituents from said fluid mixture by methane-containing vapor in a stripping zone to recover methane-rich vapor overhead and bottoms liquid containing methane and $C_2$ constituents;
   (h) partially vaporizing said stripping zone bottoms liquid to form said methane-containing vapor for said stripping zone;
   (i) separating the unvaporized stripping zone bottoms liquid from said vaporized methane-containing vapor and passing the latter to said stripping zone as said methane-containing vapor therefor; and
   (j) passing the unvaporized stripping zone bottoms liquid to said demethanizer column for fractionation therein with said first liquid fraction.

2. A process according to claim 1 wherein said cooling of the hydrocarbon feed gas mixture to condense a first liquid fraction and separation of said first liquid fraction from the cooled gas comprises the steps of: first partial cooling of said hydrocarbon feed gas mixture to condense a first portion of said first liquid fraction; separating said first portion of said first liquid fraction from the uncondensed first partial cooled gas; final partial cooling of the uncondensed first partial cooled gas to condense a second portion of said first liquid fraction; and separating said second portion of said first liquid fraction from the uncondensed final partial cooled gas.

3. A process according to claim 1 wherein said fractionation of demethanizer bottoms to recover ethylene as overhead product and ethane bottoms comprises the steps of:
   (i) providing a $C_2$ fractionation column comprising a first rectification zone, a second rectification zone having a lower end in direct heat transfer communication with an upper end of said first rectification zone, and a third rectification zone having a lower end in direct heat transfer communication with an upper end of said second rectification zone;
   (ii) rectifying said demethanizer bottoms in said first rectification zone to recover ethylene-rich overhead and ethane-rich bottoms;
   (iii) throttling said ethane-rich bottoms recovered from said first rectification zone to lower superatmospheric pressure;
   (iv) rectifying said throttled ethane-rich bottoms recovered from said first rectification zone in said second rectification zone to recover ethylene-rich overhead and ethane-rich bottoms;
   (v) throttling said ethane-rich bottoms recovered from said second rectification zone to still lower superatmospheric pressure;
   (vi) rectifying said throttled ethane-rich bottoms recovered from said second rectification zone in said third rectification zone to recover ethylene overhead and ethane bottoms;
   (vii) throttling said ethylene-rich overhead recovered from said first rectification zone and said ethylene-rich overhead recovered from said second rectification zone to said still lower superatmospheric pressure, cooling same, and passing same to an upper end of said third rectification zone as reflux to enhance the rectification therein.

4. A process according to claim 3 wherein the throttled ethylene-rich overhead recovered from said first rectification zone and ethylene-rich overhead recovered from said second rectification zone are cooled by heat exchange with said ethylene overhead recovered from said third rectification zone in said cooling of step (vii).

5. A process according to claim 1 wherein said cooling said hydrocarbon feed gas mixture to condense a first liquid fraction is to temperature below about −93° C.

6. A process according to claim 1 wherein the recovered demethanizer overhead is cooled prior to mixing with said throttled second liquid fraction.

7. A process for separating a hydrocarbon feed gas mixture comprising at least $C_1$–$C_2$ constituents including ethylene to produce a separated ethylene product, comprising the steps of:

(a) providing said hydrocarbon feed gas mixture at superatmospheric pressure between 200 and 350 psia, cooling same to condense a first liquid fraction comprising at least $C_1$–$C_2$ constituents, and separating said first liquid fraction from the uncondensed cooled gas;

(b) fractionating the first liquid fraction in a demethanizer column at superatmospheric pressure of 100 to 350 psia to recover a demethanizer overhead comprising methane and a demethanizer bottoms comprising at least $C_2$ constituents;

(c) fractionating the demethanizer bottoms in a $C_2$ fractionation column to recover ethylene as overhead product and ethane bottoms;

(d) warming the cooled gas of step (a) to substantially ambient temperature and thereafter compressing same to high superatmospheric pressure of at least 350 psia to provide warm gas at high superatmospheric pressure;

(e) further cooling the warm gas at high superatmospheric pressure to condense a second liquid fraction comprising $C_1$–$C_2$ constituents, and separating the second liquid fraction from the uncondensed further cooled gas;

(f) throttling the second liquid fraction to low superatmospheric pressure below 200 psia;

(g) mixing the throttled second liquid fraction with the demethanizer overhead to form a fluid mixture comprising $C_1$–$C_2$ constituents;

(h) stripping $C_1$ constituents from said fluid mixture by methane-containing vapor in a stripping zone to recover methane-rich vapor overhead and bottoms liquid containing methane and $C_2$ constituents;

(i) partially vaporizing said stripping zone bottoms liquid to form said methane-containing vapor for said stripping zone;

(j) separating the unvaporized stripping zone bottoms liquid from said vaporized methane-containing vapor and passing the latter to said stripping zone as said methane-containing vapor therefor; and (k) passing the unvaporized stripping zone bottoms liquid to said demethanizer column for fractionation therein with said first liquid fraction.

8. A process according to claim 7 wherein said hydrocarbon feed gas mixture contains acetylene comprising separating acetylene from said hydrocarbon feed gas mixture prior to cooling same to condense said first liquid fraction.

9. A process according to claim 7 wherein said methane-rich vapor recovered from said stripping zone is warmed by heat exchange with said warm gas at high superatmospheric pressure as part of said further cooling of the latter.

10. A process according to claim 7 wherein the further cooled gas from step (e) contains hydrogen, comprising the further steps of: cooling the further cooled gas from step (e) for partial condensation thereof, separating a hydrogen-rich vapor from the condensed liquid and warming said hydrogen-rich vapor by heat exchange with said warm gas at high superatmospheric pressure as part of said further cooling of the latter.

11. A process according to claim 10 wherein the condensed liquid from which said hydrogen-rich vapor has been separated is throttled to lower pressure and warmed by heat exchange with said warm gas at high superatmospheric pressure as part of said further cooling of the latter.

* * * * *